United States Patent [19]

Abruscato et al.

[11] Patent Number: 4,915,873
[45] Date of Patent: Apr. 10, 1990

[54] POLYMERIZATION INHIBITOR COMPOSITION FOR VINYL AROMATIC COMPOUNDS

[75] Inventors: Gerald J. Abruscato, New Britain; Paul E. Stott, Sandy Hook, both of Conn.

[73] Assignee: Uniroyal Chemical Company, Inc., Middlebury, Conn.

[21] Appl. No.: 172,048

[22] Filed: Mar. 22, 1988

Related U.S. Application Data

[63] Continuation-in-part of Ser. No. 146,913, Jan. 22, 1988, abandoned.

[51] Int. Cl.⁴ .................... C09K 15/26; C07C 7/20
[52] U.S. Cl. ........................... 252/402; 252/405; 585/5
[58] Field of Search .......................... 252/402, 405

[56] References Cited

U.S. PATENT DOCUMENTS

| | | | |
|---|---|---|---|
| 2,526,567 | 10/1950 | Drake et al. | 260/650 |
| 3,925,215 | 12/1975 | Jervis et al. | 252/402 |
| 4,061,545 | 12/1977 | Watson | 203/9 |
| 4,079,091 | 3/1978 | Matsuno | 585/5 |
| 4,105,506 | 8/1978 | Watson | 203/9 |
| 4,177,110 | 12/1979 | Watson | 203/9 |
| 4,338,474 | 7/1982 | Jackisch | 585/5 |
| 4,343,956 | 8/1982 | Jackisch | 585/5 |
| 4,457,806 | 7/1984 | Grivas et al. | 203/9 |
| 4,465,881 | 8/1984 | Miller et al. | 585/2 |
| 4,466,905 | 8/1984 | Butler et al. | 252/403 |
| 4,487,981 | 12/1984 | Miller et al. | 585/4 |
| 4,487,982 | 12/1984 | Miller et al. | 585/4 |
| 4,633,026 | 12/1986 | Kolich | 585/5 |
| 4,774,374 | 9/1988 | Abruscato et al. | 585/5 |

OTHER PUBLICATIONS

Japanese Patent Publication 40-133336, Chem Abstracts, 140737p, vol. 82, p. 17 (1975) (Yamamoto et al.).

*Primary Examiner*—John F. Terapane
*Assistant Examiner*—Valerie Denise Fee
*Attorney, Agent, or Firm*—John A. Shedden

[57] ABSTRACT

Vinyl aromatic compounds are stabilized against polymerization by the addition of an effective amount of a polymerization inhibition composition comprising (a) a phenothiazine compound; and (b) an aryl-substituted phenylenediamine compound. In other aspects, this invention is directed to a vinyl aromatic composition stabilized against polymerization by such polymerization inhibitor composition, as well as to a method of stabilizing a vinyl aromatic composition against polymerization which method comprises adding an effective amount of such polymerization inhibitor composition.

7 Claims, No Drawings

POLYMERIZATION INHIBITOR COMPOSITION FOR VINYL AROMATIC COMPOUNDS

This application is a continuation-in-part of U.S. patent application Ser. No. 146,913 filed Jan. 22, 1988, now abandoned.

FIELD OF THE INVENTION

This invention is directed to a polymerization inhibitor composition for vinyl aromatic compounds comprising (a) a phenothiazine compound; and (b) an aryl-substituted phenylenediamine compound. In other aspects, this invention is directed to a vinyl aromatic composition stabilized against polymerization by such polymerization inhibitor composition, as well as to a method of stabilizing a vinyl aromatic composition against polymerization which method comprises adding an effective amount of such polymerization inhibitor composition.

BACKGROUND OF THE INVENTION

Commercial processes for the manufacture of vinyl aromatic compounds such as monomeric styrene, divinyl benzene and lower alkylated styrenes (such as alphamethylstyrene and vinyltoluene) typically produce products contaminated with various impurities, such as benzene, toluene and the like. These impurities must be removed in order for the monomer product to be suitable for most applications. Such purification of vinyl aromatic compounds is generally accomplished by distillation.

However, it is well known that vinyl aromatic compounds polymerize readily and that the rate of polymerization increases rapidly as the temperature increases. In order to prevent polymerization of the vinyl aromatic monomer under distillation conditions various polymerization inhibitors have been employed.

In general, the compounds which are commercially employed as such polymerization inhibitors are of the U.S. Pat. No. 2,526,567, show the stabilization of nuclear chlorostyrenes employing 2,6-dinitrophenols. Similarly, U.S. Pat. No. 4,105,506, to Watson, discloses the use of 2,6-dinitro-p-cresol as a polymerization inhibitor for vinyl aromatic compounds.

In addition, it has been disclosed by Butler et al, in U.S. Pat. No. 4,466,905, that, in the presence of oxygen, the presence of phenylenediamines in the distillation column with 2,6-dinitro-p-cresol will further reduce the amount of polymerization which occurs.

While dinitrophenols are effective polymerization inhibitors, there are several disadvantages associated with their use, either alone or in blends. For example, dinitrophenols are solids that, if subjected to temperatures above their melting points, are unstable and may explode (see U.S. Pat. No. 4,457,806).

Moreover, dinitrophenols are highly toxic, many having an $LD_{50}$ (rat) of less than 30 mg/Kg (Sax, Hazardous Properties of Industrial Chemicals).

Recently, it has been disclosed by Kolich, in U.S. Pat. No. 4,633,026, that halogenated vinyl aromatic compounds (such as bromostyrene) may be inhibited from polymerizing by the addition of an amine polymerization inhibitor selected from the group consisting of certain alkyl-substituted phenylenediamine compounds and phenothiazine compounds in the presence of air.

While such prior art inhibitors may inhibit the polymerization of vinyl aromatic compounds to some degree, it would be desirable to possess polymerization inhibitors which would more effectively delay the onset of polymerization and/or which would avoid the use of highly toxic compounds such as dinitrophenols.

Accordingly, it is an object of this invention to provide an improved inhibitor composition for the prevention of polymerization of vinyl aromatic compounds.

It is an additional object of this invention to provide an inhibitor for the prevention of polymerization of vinyl aromatic compounds, which inhibitor does not comprise toxic dinitrophenolic compounds.

It is a further object of this invention to provide a vinyl aromatic composition which is stabilized against polymerization.

It is yet another object of this invention to provide an improved method for inhibiting the polymerization of vinyl aromatic compounds.

The foregoing and additional objects will become more fully apparent from the following description and accompanying Examples.

DESCRIPTION OF THE INVENTION

In one aspect, this invention is directed to a polymerization inhibitor composition comprising:

(a) a phenothiazine compound having the structure:

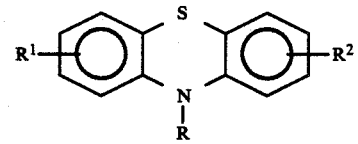

wherein R is hydrogen or $C_1$–$C_{12}$ alkyl; and $R^1$ and $R^2$ are each independently selected from the group consisting of hydrogen, $C_6$–$C_{10}$ aryl, $C_7$–$C_{11}$ aralkyl, $C_7$–$C_{16}$ alkaryl and $C_1$–$C_{12}$ alkyl; and (b) a phenylenediamine compound having the structure:

wherein
$R^3$ is $C_6$–$C_{10}$ aryl or $C_7$–$C_{16}$ alkaryl; and $R^4$, $R^5$ and $R^6$ are each independently selected from the group consisting of hydrogen, $C_1$–$C_{12}$ alkyl, $C_3$–$C_{12}$ cycloalkyl, $C_7$–$C_{11}$ aralkyl, and $C_7$–$C_{16}$ alkaryl.

In another aspect, this invention is directed to a vinyl aromatic composition stabilized against polymerization, said composition comprising:

(a) a vinyl aromatic compound; and (b) a polymerization inhibitory effective amount of a polymerization inhibitor composition comprised of:

(i) a phenothiazine compound having the structure:

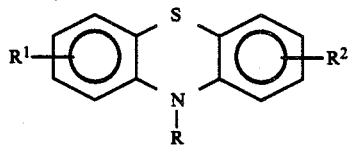

wherein R is hydrogen or $C_1$–$C_{12}$ alkyl; and $R^1$ and $R^2$ are each independently selected from the group consisting of hydrogen, $C_6$–$C_{10}$ aryl, $C_7$–$C_{11}$ aralkyl, $C_7$–$C_{16}$ alkaryl and $C_1$–$C_{12}$ alkyl; and (ii) a phenylenediamine compound having the structure:

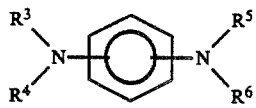

wherein $R^3$ is $C_6$–$C_{10}$ aryl or $C_7$–$C_{16}$ alkaryl; and $R^4$, $R^5$ and $R^6$ are each independently selected from the group consisting of hydrogen, $C_1$–$C_{12}$ alkyl, $C_3$–$C_{12}$ cycloalkyl, $C_7$–$C_{11}$ aralkyl, and $C_7$–$C_{16}$ alkaryl.

In yet another aspect, this invention is directed to a method for inhibiting the polymerization of a vinyl aromatic compound, which method comprises adding a polymerization inhibiting effective amount of a polymerization inhibitor composition comprising:

(a) a phenothiazine compound having the structure:

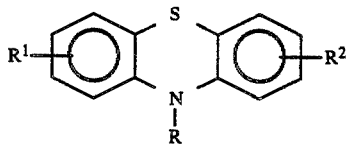

wherein R is hydrogen or $C_1$–$C_{12}$ alkyl; and $R^1$ and $R^2$ are each independently selected from the group consisting of hydrogen, $C_6$–$C_{10}$ aryl, $C_7$–$C_{11}$ aralkyl, $C_7$–$C_{16}$ alkaryl and $C_1$–$C_{12}$ alkyl; and (b) a phenylenediamine compound having the structure:

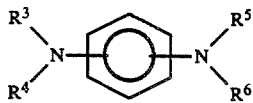

wherein $R^3$ is $C_6$–$C_{10}$ aryl or $C_7$–$C_{16}$ alkaryl; and $R^4$, $R^5$ and $R^6$ are each independently selected from the group consisting of hydrogen, $C_1$–$C_{12}$ alkyl, $C_3$–$C_{12}$ cycloalkyl, $C_7$–$C_{11}$ aralkyl, and $C_7$–$C_{16}$ alkaryl.

The vinyl aromatic polymerization inhibitory compositions of this invention are comprised of (a) a phenothiazine compound: and (b) an aryl-substituted phenylenediamine compound.

The phenothiazine compounds which may be employed are of the structural formula:

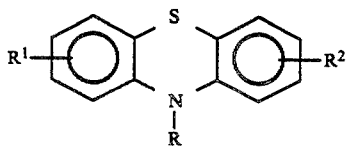

wherein R is hydrogen or $C_1$–$C_{12}$ alkyl; and $R^1$ and $R^2$ are each independently selected from the group consisting of hydrogen, $C_6$–$C_{10}$ aryl, $C_7$–$C_{11}$ aralkyl, $C_7$–$C_{16}$ alkaryl and $C_1$–$C_{12}$ alkyl. Particularly suitable phenothiazine compounds which can be employed herein include phenothiazine, 2-methylphenothiazine, 2-octyl-phenothiazine, 2-nonylphenothiazine, 2,8-dimethylphenothiazine, 3,7-dimethylphenothiazine, 3,7-diethylphenothiazine, 3,7-dibutylphenothiazine, 3,7-dioctylphenothiazine, 2,8-dioctylphenothiazine, 3,7-dinonylphenothiazine, 2,8-dinonylphenothiazine, 2(alpha,alpha-dimethylbenzyl)phenothiazine, 3,7-bis(alpha,alpha-dimethylbenzyl)phenothiazine, 2,8-bis(alpha,alpha-dimethylbenzyl)phenothiazine, N-methyl-2,8-dioctylphenothiazine and N-methyl-3,7-dioctylphenothiazine. Moreover, mixtures of two or more phenothiazine compounds may also be employed.

The phenylenediamine compounds which may be employed possess the structural formula:

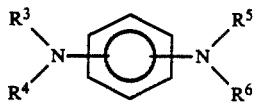

wherein $R^3$ is $C_6$–$C_{10}$ aryl or $C_7$–$C_{16}$ aralkyl: and $R^4$, $R^5$ and $R^6$ are each independently selected from the group consisting of hydrogen, $C_1$–$C_{12}$ alkyl, $C_3$–$C_{12}$ cycloalkyl, $C_7$–$C_{11}$ aralkyl and $C_7$–$C_{16}$ alkaryl Preferred compounds include those wherein the amine groups are in the para position. Particularly preferred compounds are para-phenylenediamines wherein $R^4$ and $R^5$ are hydrogen; $R^3$ is phenyl; and $R^6$ is $C_3$–$C_8$ alkyl or $C_3$–$C_8$ cycloalkyl.

Illustrative preferred phenylenediamine compounds which may be employed include N-phenyl-N'-isopropyl-p-phenylenediamine, N-phenyl-N'-(1,3-dimethylbutyl)-p-phenylenediamine, N-phenyl-N'-(1,4-dimethylpentyl)-p-phenylenediamine and N-phenyl-N'-cyclohexyl-p-phenylenediamine. Moreover, mixtures of phenylenediamine compounds may be employed. The phenylenediamine compounds may be of the oxygenated species described in copending U.S. patent application No. 061,855, filed June 12, 1987.

The phenothiazine and phenylenediamine compounds are generally employed in weight ratios of between about 10:1 and about 1:10. Preferably, weight ratios of between about 4:1 and about 1:4 are employed, with ratios of between about 2:1 and about 1:2 being particularly preferred.

The polymerization inhibitor compositions of this invention may further comprise an aromatic hydrocarbon solvent. Illustrative of such solvents are benzene, toluene, xylene, ethylbenzene and other alkyl-benzenes as well as vinyl aromatic compounds themselves such as styrene, alphamethylstyrene and the like. Typically, when solvents are employed the hydrogenated precursors of the vinyl aromatic to be stabilized are the preferred solvents. Thus, for the stabilization of styrene, ethylbenzene is the preferred solvent. Similarly for the stabilization of alpha-methylstyrene, isopropylbenzene is the preferred solvent.

The vinyl aromatic composition of this invention is comprised of (a) a vinyl aromatic compound; and (b) a polymerization inhibitory effective amount of the polymerization inhibitor compound described above.

Illustrative of the vinyl aromatic compounds which may be stabilized against polymerization by the process of this invention are styrene, alpha-methylstyrene, vinyltoluene and divinylbenzene, as well as halogenated species thereof.

The stabilized vinyl aromatic composition of this invention may be in the form of a reaction mixture additionally comprising the starting materials of the vinyl aromatic compound to be stabilized as well as byproducts of the production process. Thus, in the case of styrene, the reaction mixture will typically include starting materials such as benzene, ethylbenzene and ethylene, as well as byproducts such as diethylbenzene, vinyl toluene and the like.

The primary use of the polymerization inhibitor compositions of tis invention is to prevent the polymerization of vinyl aromatics during purification/distillation to remove unreacted starting materials and distillable byproducts. Typically, this involves the sequential distillation of the vinyl aromatic reaction product through a plurality of distillation columns. In the first of such columns, a relatively large amount of starting material and byproducts will be present, while in the last column essentially pure vinyl aromatic compound (plus polymerization inhibitors and heavy, nondistillable byproducts) will be present.

The method of this invention involves adding to a vinyl aromatic compound an effective amount of the polymerization inhibitor composition of this invention. When the polymerization inhibitor composition of this invention is employed during the purification/distillation of vinyl aromatic compounds, it is preferred that oxygen, whether in the form of air or otherwise, be present. It is also noted that the polymerization inhibitor composition of this invention will be effective for uses other than during distillation—e.g., during the shipment or storage of vinyl aromatic compounds.

The vinyl aromatic composition and method of this invention comprise or involve the addition of an effective amount of polymerization inhibitor composition. As employed herein, the term "effective amount" refers to that amount of inhibitor composition which is needed to prevent the formation of more than about 1 weight percent of vinyl aromatic polymer in less than about 3 hours at temperatures of between about 90° and about 150° C. Although the amount of polymerization inhibitor required will vary somewhat (based upon such factors as the particular vinyl aromatic compound stabilized; the particular phenylenediamine and phenothiazine species employed; and the like) such an effective amount may be readily determined by routine experimentation. In general, such an effective amount will be between about 50 and about 1,500 parts per million by weight of vinyl aromatic compound.

The polymerization inhibitor composition of this invention will provide stability against vinyl aromatic polymerization at temperatures typically employed for the purification of vinyl aromatic compound (e.g., of between about 90° and about 140° C.) for periods well in excess of those typically employed for such purification. This stability is achieved without the use of undesirably toxic dinitrophenolic compounds which are generally employed in commercial operations today.

EXAMPLES

The following Examples are intended to further illustrate the present invention and are not intended to limit the scope of the invention in any manner whatsoever.

EXAMPLES 1 AND 2 AND COMPARATIVE EXPERIMENT A

To a fifty milliliter flask (Example 1) charged with forty grams of styrene were added 50 ppm of 4-isopropylaminodiphenylamine and 50 ppm of phenothiazine. The flask was fitted with a magnetic stirrer and septum closure and heated in an oil bath to 118° C. (plus or minus 2° C.). The flask was purged with approximately 5 cc/min air run beneath the liquid surface during the period of the test. During the test period, samples were removed from the flask every one-half hour and tested for degree of polymerization by measuring the changes in refractive index. The time until onset of polymerization, defined as the point at which 1 weight percent of the styrene had polymerized, was determined to be 4 hours.

Employing this procedure, a second aryl-substituted phenylenediamine, N-(1,4-dimethylpentyl)-N'-phenyl-p-phenylenediamine, was similarly tested in combination with phenothiazine (Example 2).

In order to compare these results with prior art vinyl aromatic polymerization inhibitors, a third flask (Comparative Experiment A) was prepared comprising 50 ppm of phenothiazine plus 50 ppm of a non-aryl substituted phenylenediamine compound, N,N'(p-phenylene)bis(2-amino-5-methylhexane), in 40 grams of styrene. This flask was tested in accordance with the procedure described for Example 1. It is noted that U.S. Pat. No. 4,633,026 to Kolich indicates that vinyl aromatic compounds may be stabilized against polymerization with amines selected from the group consisting of phenothiazines and non-aryl-substituted phenylenediamines.

The results of such testing are summarized in Table I below.

TABLE 1

| Example or Comparative Experiment | Aryl-substituted Phenylenediamine Co-inhibitor* | Time (Hrs) to Onset of Polymerization |
|---|---|---|
| 1 | Yes | 4 |
| 2 | Yes | 3.5 |
| A | No | 1.5 |

*In combination with phenothiazine.

The above data indicate the unexpected degree of polymerization inhibition afforded by the inhibitor compositions of this invention.

EXAMPLES 3-5

Employing a process essentially identical to that described in Example 1 above, several akylated phenothiazines were tested (at a concentration of 50 parts per million (ppm) by weight, based upon the weight of styrene employed) in combination with 4-isopropylamino diphenylamine (at 50 ppm) for their effectiveness as polymerization inhibitors. The results of such testing are summarized in Table 2.

TABLE 2

| Example | Phenothiazine | Time (hours) to Onset of Polymerization* |
|---|---|---|
| 3 | 3,7-dinonyl phenothiazine | 4.5 |
| 4 | 3,7-diocty phenothiazine | 4.5 |
| 5 | N-methyl-3,7- | 4.5 |

TABLE 2-continued

| Example | Phenothiazine | Time (hours) to Onset of Polymerization* |
|---|---|---|
| | dioctyl phenothiazine | |

*Point at which 1 weight percent of the styrene had polymerized.

The above results further indicate the desirable polymerization inhibitory activity of the compositions of this invention.

What is claimed is:

1. A polymerization inhibitor composition comprising:

(a) a phenothiazine compound having the structure:

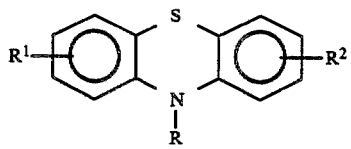

wherein R is hydrogen or $C_1$–$C_{12}$ alkyl; and $R^1$ and $R^2$ are each independently selected from the group consisting of hydrogen, $C_6$–$C_{10}$ aryl, $C_7$–$C_{11}$ aralkyl, $C_7$–$C_{16}$ alkaryl and $C_1$–$C_{12}$ alkyl; and (b) a phenylenediamine compound having the structure:

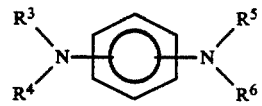

wherein
   $R^3$ is $C_6$–$C_{10}$ aryl or $C_7$–$C_{16}$ alkaryl; and
   $R^4$, $R^5$ and $R^6$ are each independently selected from the group consisting of hydrogen, $C_1$–$C_{12}$ alkyl, $C_3$–$C_{12}$ cycloalkyl, $C_7$–$C_{11}$ aralkyl, and $C_7$–$C_{16}$ alkaryl.

2. A composition in accordance with claim 1 wherein component (a) is selected from the group consisting of phenothiazine, 2-methylphenothiazine, 2-octylphenothiazine, 2-nonylphenothiazine, 2,8-dimethylphenothiazine, 3,7-dimethylphenothiazine, 3,7-diethylphenothiazine, 3,7-dibutylphenothiazine, 3,7-dioctylphenothiazine, and 2,8-dioctylphenothiazine, 3,7-dinonylphenothiazine, 2,8-dinonylphenothiazine, 2(alpha,alpha-dimethylbenzyl)phenothiazine, 3,7-bis(alpha,alpha-dimethylbenzyl)phenothiazine, 2,8-bis(alpha,alpha-dimethylbenzyl)phenothiazine, N-methyl-3,7-dioctylphenothiazine and N-methyl-2,8-dioctylphenothiazine.

3. A composition in accordance with claim 1 wherein component (b) is a para-phenylenediamine compound wherein $R^4$ and $R^5$ are hydrogen; $R^3$ is phenyl; and $R^6$ is $C_3$–$C_8$ alkyl or $C_3$–$C_8$ cycloalkyl.

4. A composition in accordance with claim 1 wherein the weight ratio of component (a) to component (b) is between about 10:1 and about 1:10.

5. A composition in accordance with claim 4 wherein the weight ratio of component (a) to component (b) is between about 4:1 and about 1:4.

6. A composition in accordance with claim 5 wherein the weight ratio of component (a) to component (b) is between about 2:1 and about 1:2.

7. A composition in accordance with claim 1 wherein said composition further comprises a solvent.

* * * * *